United States Patent
Lagrange et al.

[11] Patent Number: 5,984,975
[45] Date of Patent: *Nov. 16, 1999

[54] 3-SUBSTITUTED PARA-AMINOPHENOLS AND USE THEREOF IN DYEING KERATINOUS FIBERS

[75] Inventors: Alain Lagrange, Coupvray; Jean Jacques Vandenbosche, Sevran; Jean Cotteret, Verneuil-sur-Seine; Marie Pascale Audousset, Levallois-Perret, all of France

[73] Assignee: L'oreal, Paris, France

[*] Notice: This patent is subject to a terminal disclaimer.

[21] Appl. No.: 08/868,540

[22] Filed: Jun. 4, 1997

Related U.S. Application Data

[62] Continuation of application No. 08/759,843, Dec. 2, 1996, Pat. No. 5,703,266, which is a continuation of application No. 08/374,694, filed as application No. PCT/FR94/00606, May 24, 1994, abandoned.

[30] Foreign Application Priority Data

May 25, 1993 [FR] France ..................... 9306231

[51] Int. Cl.$^6$ ............. A61K 7/13; C07C 215/76
[52] U.S. Cl. ............. 8/412; 8/406; 8/407; 8/408; 8/421; 558/418; 558/423
[58] Field of Search ................. 8/405, 406, 408, 8/409, 410, 411, 412, 421, 407; 558/418, 423

[56] References Cited

U.S. PATENT DOCUMENTS

| | | | |
|---|---|---|---|
| 696,020 | 3/1902 | Eichengrun et al. | 564/443 |
| 3,053,895 | 9/1962 | Kaeding | 564/443 |
| 3,546,343 | 12/1970 | Payne et al. | 514/483 |
| 3,918,896 | 11/1975 | Kalopissis et al. | 8/409 |
| 4,065,255 | 12/1977 | Andrillon et al. | 8/412 |
| 4,238,400 | 12/1980 | Yelland | 552/231 |
| 4,330,291 | 5/1982 | Bugaut et al. | 8/406 |
| 4,420,637 | 12/1983 | Bugaut et al. | 8/406 |
| 4,473,374 | 9/1984 | Bugaut et al. | 8/405 |
| 4,713,383 | 12/1987 | Francis et al. | 514/267 |
| 4,797,130 | 1/1989 | Clausen et al. | 8/421 |
| 4,883,656 | 11/1989 | Konrad et al. | 8/408 |
| 4,888,025 | 12/1989 | Bugaut et al. | 8/405 |
| 4,997,451 | 3/1991 | Clausen et al. | 8/421 |
| 5,019,642 | 5/1991 | Hashimoto | 528/353 |
| 5,034,014 | 7/1991 | Wenke | 8/408 |
| 5,047,066 | 9/1991 | Mano et al. | 8/421 |
| 5,053,052 | 10/1991 | Junino et al. | 8/412 |
| 5,073,173 | 12/1991 | Pan et al. | 8/405 |
| 5,084,067 | 1/1992 | Junino et al. | 8/421 |
| 5,183,941 | 2/1993 | Pan et al. | 564/390 |
| 5,202,487 | 4/1993 | Junino et al. | 8/411 |
| 5,344,463 | 9/1994 | Chan et al. | 8/408 |
| 5,409,503 | 4/1995 | Clausen et al. | 8/408 |

FOREIGN PATENT DOCUMENTS

| | | |
|---|---|---|
| 0085890 | 8/1983 | European Pat. Off. . |
| 0241716 | 10/1987 | European Pat. Off. . |
| 0331144 | 9/1989 | European Pat. Off. . |
| 2421870 | 12/1979 | France . |

OTHER PUBLICATIONS

Patent Abstracts of Japan, Abstract of JP 1022972, Kao Corp., Jan. 1989.

*Primary Examiner*—Caroline D. Liott
*Attorney, Agent, or Firm*—Jacobson, Price, Holman & Stern, PLLC

[57] ABSTRACT

A method or composition for dyeing keratinous fibres using as an oxidation dye precursor a 3-substituted para-aminophenol of formula:

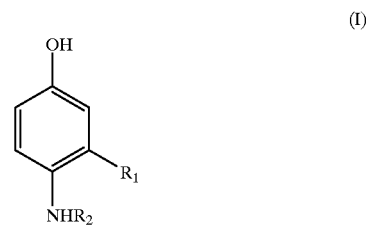

(I)

where $R_1$ represents alkyl, alkenyl, mono- or polyhydroxyalkyl, cyano, cyanoalkyl, halogenoalkyl, aminoalkyl or alkoxyalkyl and $R_2$ represents hydrogen, alkyl or mono- or polyhydroxyalkyl, provided that when $R_2$ is hydrogen $R_1$ is not methyl or trifluoromethyl, and addition salts thereof with an acid.

16 Claims, No Drawings

3-SUBSTITUTED PARA-AMINOPHENOLS AND USE THEREOF IN DYEING KERATINOUS FIBERS

This is a continuation application of Ser. No. 08/759,843, filed Dec. 2, 1996, now U.S. Pat. No. 5,703,266, which is a continuation application of Ser. No. 08/374,694, filed Jan. 25, 1995, abandoned, which is a 371 of PCT/FR94/00606, May 24, 1994.

The invention concerns the use of 3-substituted para-aminophenols in dye compositions for dyeing keratinous fibres, in particular human hair, these dye compositions being for use in oxidation dyeing or permanent dyeing, and 3-substituted para-aminophenols.

Dyeing keratinous fibres by oxidation dyeing uses oxidation dye precursors which are also known as oxidation bases. These are colourless but when brought into contact with an oxidising agent develop a durable colour in the keratinous fibres.

Substituted and unsubstituted para-phenylene-diamines, ortho-phenylenediamines, para-aminophenols and ortho-aminophenols are known oxidation dye precursors. These dye precursors can be mixed with one or more "couplers" which vary the shades obtained with the dye precursors. These couplers are generally selected from metaphenylenediamines, metaaminophenols, metadiphenols and phenols.

In the art of dyeing keratinous fibres, especially human hair, oxidation dye precursors are always being sought which, when associated with couplers, will produce a colour in the hair which is satisfactorily resistant to light, washing, inclement weather, perspiration and various treatments that can be applied to the hair. Such oxidation dye precursors must also be harmless.

We have now discovered, and this forms the subject matter of the invention, that the use of certain 3-substituted para-aminophenols as oxidation dye precursors in dye compositions for keratinous fibres produces in the latter, in particular in human hair, colours with good resistance to light, washing, inclement weather, perspiration and various treatments which can be applied to the hair, in particular light and inclement weather. The colours obtained are less selective, i.e. substantially the same on natural hair and on hair which has been sensitised by a treatment such as bleaching or perming, resulting in high uniformity of colour from the (natural) root to the (sensitised) tip of the hair. The 3-substituted para-aminophenols are also harmless.

The invention consists in the use of 3-substituted para-aminophenols with formula (I) as defined below in the dyeing of keratinous fibres, in particular human hair.

The invention also consists in dye compositions for keratinous fibres, in particular human hair, containing, in an appropriate dye medium, at least one 3-substituted para-aminophenol with formula (I):

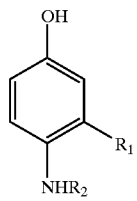

(I)

where $R_1$ represents a $C_1$–$C_4$ alkyl radical, a $C_2$–$C_4$ alkenyl radical, a $C_1$–$C_6$ monohydroxyalkyl radical, a $C_2$–$C_6$ polyhydroxyalkyl radical, a $C_2$–$C_6$ alkoxyalkyl radical, a cyano radical, a $C_1$–$C_4$ cyanoalkyl radical, a $C_1$–$C_4$ halogenoalkyl radical, preferably a $C_1$–$C_4$ fluoroalkyl radical, an aminoalkyl radical with formula:

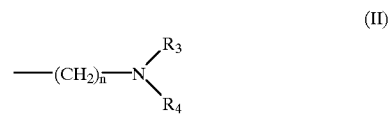

(II)

where:
 n is a whole number from 1 to 6 inclusive;
 $R_3$ and $R_4$, which may be identical or different, represent a hydrogen atom or a $C_1$–$C_4$ alkyl, $C_1$–$C_4$ hydroxyalkyl or $C_1$–$C_6$ acyl radical;
 $R_2$ represents a hydrogen atom, a $C_1$–$C_6$ alkyl radical, a $C_1$–$C_6$ monohydroxyalkyl radical or a $C_2$–$C_6$ polyhydroxyalkyl radical, provided that:
  when $R_2$ is hydrogen, $R_1$ does not represent methyl or trifluoromethyl,
 or an addition salt thereof with an acid.

The following particular examples of compounds with formula (I) may be cited:
3-ethyl p-aminophenol,
3-hydroxymethyl p-aminophenol,
3-cyanomethyl p-aminophenol,
3-tert-butyl p-aminophenol,
3-(β-methoxyethyl) p-aminophenol,
3-(β-ethoxyethyl) p-aminophenol.

The invention further consists in a method of dyeing keratinous fibres, in particular human hair, using a dye composition as defined above mixed with an oxidising agent.

The invention still further consists in novel 3-substituted para-aminophenols.

Further objects of the invention will become apparent from the following description and examples.

Novel 3-substituted para-aminophenols in accordance with the invention have formula:

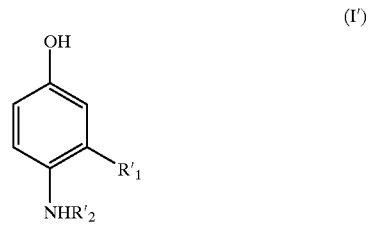

(I')

where $R'_1$ and $R'_2$ have the meanings given for $R_1$ and $R_2$ above, except that:
 when $R'_2$ represents a hydrogen atom, $R'_1$ does not represent an alkyl, vinyl, dichloromethyl or trifluoromethyl radical;
 when $R'_1$ represents a methyl radical, $R'_2$ does not represent an ethyl radical.

The compounds of the invention can also be addition salts of compounds with formula (I') above with an acid.

The following 3-substituted para-aminophenols with formula (I') may be cited:
3-hydroxymethyl p-aminophenol,
3-cyanomethyl p-aminophenol,
3-(β-methoxyethyl) p-aminophenol,
3-(β-ethoxyethyl) p-aminophenol, and in particular 3-hydroxymethyl p-aminophenol.

The alkyl radical in formulae (I) and (I') above preferably represents methyl, ethyl, propyl, isopropyl, butyl, sec-butyl, tert-butyl; the mono- or polyhydroxy-alkyl radical preferably represents:

—CH$_2$OH, —CH$_2$—CH$_2$OH, —CH$_2$CHOH—CH$_2$—OH, —CH$_2$—CHOH—CH$_3$;

the alkoxyalkyl radical preferably represents:

—CH$_2$CH$_2$OCH$_3$, —CH$_2$CH$_2$OC$_2$H$_5$;

the aminoalkyl radical preferably represents:

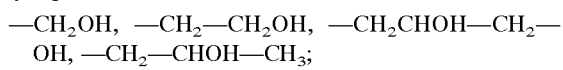

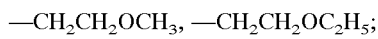

when radicals R$_3$ and R$_4$ represent an acyl radical, this preferably represents the formyl, acetyl and propionyl radicals.

Examples of fluoroalkyl radicals which may be cited are the trifluoromethyl and trifluoroethyl radicals.

Corresponding acid salts of compounds with formulae (I) or (I') are preferably selected from hydrochlorides, sulphates and hydrobromides.

Novel compounds with formula (I') are those where R'$_2$=H and are prepared by one of the following methods:

1) Nitrosation of the 3- substituted phenol corresponding to the desired p-aminophenol using sodium or potassium nitrite or an alkal ine-earth metal in alkaline medium, followed by hydrogenation of the nitroso group by sodium hydrosulphite in alkaline medium in the presence of hydrogen and transition metals such as platinum or palladium.

This method of preparation corresponds to the following reaction scheme:

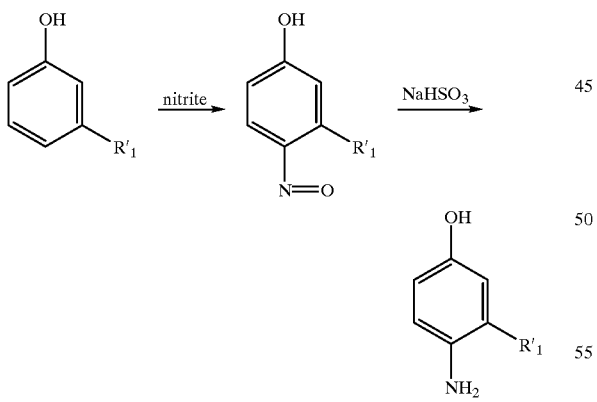

2) Reduction of the nitro group of a 2-substituted nitrobenzene to produce an arylhydroxylamine, either using aluminium in an aqueous acidified medium, or in the presence of hydrogen in an aqueous acidified medium and a platinum type catalyst, followed by a BAMBERGER rearrangement in the presence of an acid in accordance with the reaction scheme described in "Advanced Organic Chemistry", p 606.

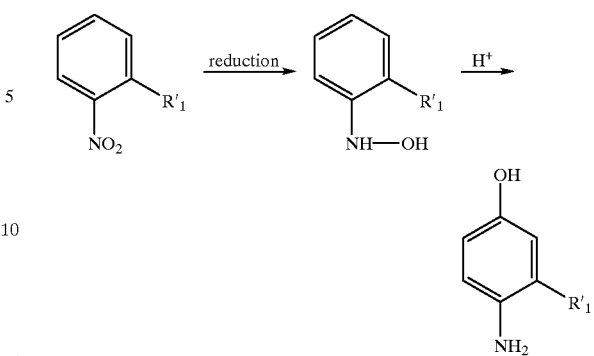

3) Condensation of a diazonium salt of p-sulphanilic acid with the 3-substituted phenol corresponding to the desired p-aminophenol, followed by reduction of the azo compound produced using sodium hydrosulphite in an aqueous medium in the presence of hydrogen and transition metals such as platinum or palladium, in accordance with the following reaction scheme:

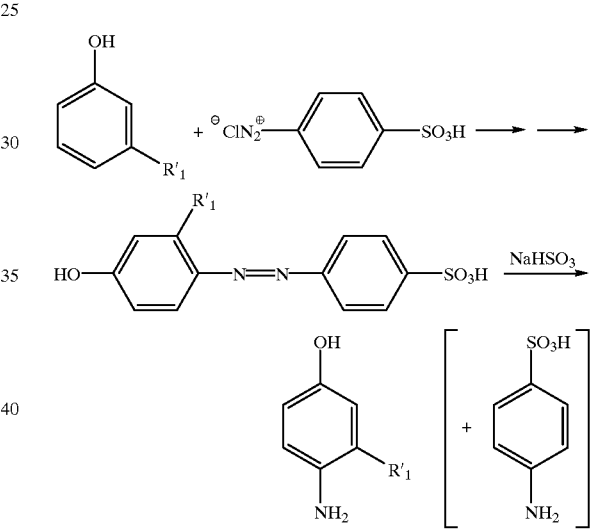

4) Reduction of the nitro group and cleavage of the benzyloxy (BzO) group in a compound with formula:

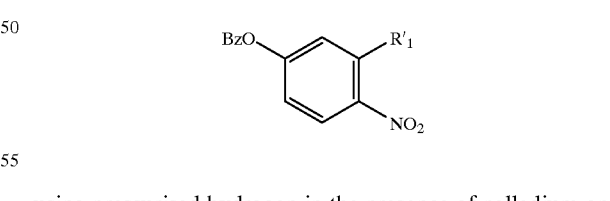

using pressurised hydrogen in the presence of palladium on activated carbon in cyclohexene.

Compounds with formula (I') where R'$_2$ is not a hydrogen atom are obtained using conventional aromatic amine alkylation and hydroxyalkylation methods.

Compounds with formula (I) in dye compositions in accordance with the invention are generally used in the presence of a coupler selected from metadiphenols, metaaminophenols and metaphenylenediamines such as those with formula (III):

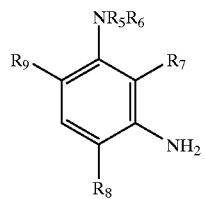

(III)

where:
- $R_5$ and $R_6$ independently represent a hydrogen atom, a $C_1-C_4$ alkyl or $C_1-C_4$ hydroxyalkyl group;
- $R_7$ represents a hydrogen atom or a $C_1-C_4$ alkyl or alkoxy group;
- $R_8$ represents a hydrogen atom or a $C_1-C_4$ alkyl, $C_1-C_4$ hydroxyalkoxy or $C_1-C_4$ alkoxy group;
- $R_9$ represents a hydrogen or halogen atom or a $C_1-C_4$ alkyl, $C_1-C_4$ alkoxy, $C_1-C_4$ hydroxyalkyl, $C_1-C_4$ hydroxy-alkoxy, $C_2-C_4$ polyhydroxyalkoxy, $C_1-C_4$ carboxyalkoxy, $C_1-C_4$ 2',4'-diaminophenoxyalkoxy or $C_1-C_4$ aminoalkoxy group;
- provided that, when $R_9$ represents a carboxyalkoxy or 2',4'-diaminophenoxyalkoxy group, $R_5$, $R_6$, $R_7$ and $R_8$ represent hydrogen, and salts thereof, also metaacylaminophenols, metaureidophenols, metacarbalkoxyaminophenols, α-naphthol, indole derivatives, and couplers containing an active methylene group such as β-ketones and pyrazolones.

The following couplers may in particular be cited:
2,4-dihydroxyphenoxyethanol,
2,4-dihydroxyanisole,
metaaminophenol,
resorcin monomethylether,
resorcin,
2-methylresorcin,
2-methyl 5-aminophenol,
2-methyl 5-N-(β-hydroxyethyl) aminophenol,
2-methyl 5-N-(β-mesylaminoethyl)aminophenol,
2,6-dimethyl 3-aminophenol,
6-hydroxybenzomorpholine,
2,4-diaminoanisole,
2,4-diaminophenoxyethanol,
6-aminobenzomorpholine,
[2-N-(β-hydroxyethyl) amino 4-amino]-phenoxyethanol,
2-hydroxy 4-N-(β-hydroxyethyl) aminoanisole,
2-amino 4-N-(β-hydroxyethyl) aminoanisole,
(2,4-diamino) phenyl-β,γ-dihydroxypropylether,
(2,4-diamino) phenyl-α,β-dihydroxypropylether,
1-[2',4'-diaminophenoxypropyloxy] 2,4-diaminobenzene,
2,4-diaminophenoxyacetic acid,
2,4-diaminophenoxyethylamine,
1,3-dimethoxy 2,4-diaminobenzene,
1,3,5-trimethoxy 2,4-diaminobenzene,
1-amino 3,4-methylenedioxybenzene,
1-hydroxy 3,4-methylenedioxybenzene,
2-chloro 6-methyl 3-aminophenol,
2-methyl 3-aminophenol,
2-chlororesorcinol,
6-methoxy 3-hydroxyethylaminoaniline,
1-ethoxy 2-bis(β-hydroxyethyl)amino 4-aminobenzene,
3-diethylaminophenol,
1,3-dihydroxy 2-methylbenzene,
1-hydroxy 2,4-dichloro 3-aminobenzene,
4,6-bis-(β-hydroxyethoxy) 1,3-diaminobenzene,
4-methyl 6-ethoxy 1,3-diaminobenzene,
4-chloro 6-methyl 3-aminophenol,
6-chloro 3-trifluoroethylaminophenol,
6-hydroxyindole,
7-hydroxyindole,
4-hydroxyindole,
7-aminoindole,
5,6-dihydroxyindole, and derivatives thereof such as those described in French patent documents FR-A-2 636 236, FR-A-2 654 335, FR-A-2 654 336, FR-A-2 659 228, FR-A-2 664 304, FR-A-2 664 305 and FR-A-2 671 722.

In addition to 3-substituted para-aminophenols with formula (I), dye compositions in accordance with the invention may contain other known para and/or ortho oxidation dye precursors.

These ortho or para type oxidation dye precursors are benzene or heterocyclic compounds containing two amino or hydroxy and amino functional groups in ortho or para positions relative to each other.

Ortho or para type oxidation dye precursors may be selected from paraphenylenediamines, paraaminophenols other than those with formula (I), para heterocyclic precursors derived from pyridine or pyrimidine such as 2,5-diaminopyridine, 2-hydroxy 5-aminopyridine, 2,4,5,6-tetraaminopyridine, 4,5-diamino 1-methylpyrazole, 2-dimethylamino 4,5,6-triaminopyrimidine, orthoaminophenols and "double" bases.

Particular paraphenylenediamines are compounds with formula (IV):

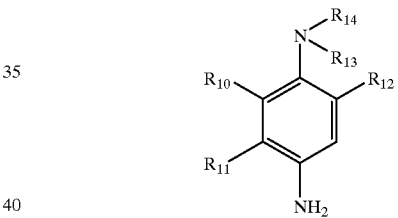

(IV)

where:
- $R_{10}$, $R_{11}$, and $R_{12}$, which may be identical or different, represent a hydrogen or halogen atom, an alkyl radical, an alkoxy radical, or a carboxy, sulpho or $C_1-C_4$ hydroxyalkyl radical;
- $R_{13}$ and $R_{14}$, which may be identical or different, represent a hydrogen atom, an alkyl, hydroxyalkyl, alkoxyalkyl, carbamylalkyl, mesylaminoalkyl, acetylaminoalkyl, ureidoalkyl, carbalkoxyaminoalkyl, sulphoalkyl, piperidinoalkyl, morpholinoalkyl or phenyl radical which latter may substituted in the para position by an amino group; or
- $R_{13}$ and $R_{14}$, together with the nitrogen atom to which they are bonded, form a piperidino or morpholino heterocycle, provided that $R_{10}$ or $R_{12}$ represent a hydrogen atom when $R_{13}$ and $R_{14}$ do not represent a hydrogen atom, and salts of these compounds. The alkyl or alkoxy radicals preferably contain one to four carbon atoms and in particular designate a methyl, ethyl, propyl, methoxy or ethoxy radical.

The following compounds with formula (IV) may in particular be cited:
paraphenylenediamine,
paratoluylenediamine,
methoxyparaphenylenediamine, chloroparaphenylenediamine,
2,3-dimethylparaphenylenediamine,
2,6-dimethylparaphenylenediamine,
2,6-diethylparaphenylenediamine,
2,5-dimethylparaphenylenediamine,
2-methyl 5-methoxyparaphenylenediamine,
2,6-dimethyl 5-methoxyparaphenylenediamine,
N,N-dimethylparaphenylenediamine,
N,N-diethylparaphenylenediamine,
N,N-dipropylparaphenylenediamine,
3-methyl 4-amino N,N-diethylaniline,
N,N-di-(β-hydroxyethyl)paraphenylenediamine,
3-methyl 4-amino N,N-di-(β-hydroxyethyl) aniline,
3-chloro 4-amino N,N-di-(β-hydroxyethyl) aniline,
4-amino N,N-(ethyl, carbamylmethyl) aniline,
3-methyl 4-amino N,N-(ethyl, carbamylmethyl) aniline,
4-amino N,N-(ethyl, β-piperidinoethyl) aniline,
3-methyl 4-amino N,N-(ethyl, β-piperidinoethyl) aniline,
4-amino N,N-(ethyl, β-morpholinoethyl) aniline,
3-methyl 4-amino N,N-(ethyl, β-morpholinoethyl) aniline,
4-amino N,N-(ethyl, β-acetylaminoethyl) aniline,
4-amino N-(β-methoxyethyl) aniline,
3-methyl 4-amino N,N-(ethyl, β-acetylaminoethyl) aniline,
4-amino N,N-(ethyl, β-mesylaminoethyl) aniline,
3-methyl 4-amino N,N-(ethyl, β-mesylaminoethyl) aniline,
4-amino N,N-(ethyl, β-sulphoethyl) aniline,
3-methyl 4-amino N,N-(ethyl, β-sulphoethyl) aniline,
N-[(4'-amino)phenyl] morpholine,
N-[(4'-amino)phenyl] piperidine,
2-β-hydroxyethylparaphenylenediamine,
fluoroparaphenylenediamine,
carboxyparaphenylenediamine,
sulphoparaphenylenediamine,
2-isopropylparaphenylenediamine,
2-n-propylparaphenylenediamine,
hydroxy-2-n-propylparaphenylenediamine,
2-hydroxymethylparaphenylenediamine,
N,N-dimethyl 3-methylparaphenylenediamine,
N,N-(ethyl, β-hydroxyethyl)paraphenylenediamine,
N-(dihydroxypropyl)paraphenylenediamine,
N-4'-aminophenylparaphenylenediamine,
N-phenylparaphenylenediamine.

These paraphenylenediamines may be used either as the free base or in their salt form such as the hydrochloride, hydrobromate or sulphate.

The following p-aminophenols other than those with formula (I) may be cited:
p-aminophenol,
2-methyl 4-aminophenol,
3-methyl 4-aminophenol,
2-chloro 4-aminophenol,
3-chloro 4-aminophenol,
2,6-dimethyl 4-aminophenol,
3,5-dimethyl 4-aminophenol,
2,3-dimethyl 4-aminophenol,
2,5-dimethyl 4-aminophenol,
2-hydroxymethyl 4-aminophenol,
2-(β-hydroxyethyl) 4-aminophenol,
2-methoxy 4-aminophenol,
3-methoxy 4-aminophenol,
3-(β-hydroxyethoxy)) 4-aminophenol,
2-aminomethyl 4-aminophenol,
2-β-hydroxyethylaminomethyl 4-aminophenol and those with formula (V) below:

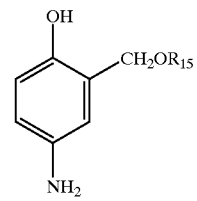

(V)

where $R_{15}$ represents a $C_1$–$C_6$ alkyl radical, a $C_1$–$C_6$ hydroxyalkyl radical, a $C_2$–$C_6$ polyhydroxylkyl radical, a $C_1$–$C_6$ halogenoalkyl radical, a $C_2$–$C_4$ aminoalkyl radical, a $C_2$–$C_4$ aminoalkyl radical where the amine is mono substituted or disubstituted by a $C_1$–$C_4$ alkyl group or substituted by a $C_3$–$C_4$ dihydroxyalkyl group and salts thereof.

The following compounds with formula (V) may in particular be cited:
2-methoxymethyl 4-aminophenol,
2-ethoxymethyl 4-aminophenol,
2-n-propyloxymethyl 4-aminophenol,
2-isopropyloxymethyl 4-aminophenol,
2-(β-hydroxyethoxy)methyl 4-aminophenol,
2-[(2',2',2'-trifluoroethoxy)methyl] 4-aminophenol, and salts thereof.

The "double" bases are bis-phenylalkylenediamines with formula:

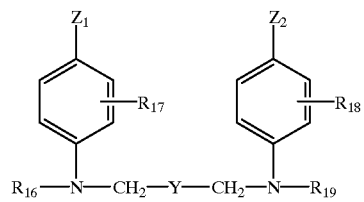

(VI)

where:
$Z_1$ and $Z_2$, which may be identical or different, represent hydroxy or $NHR_{20}$ groups, where $R_{20}$ represents a hydrogen atom or a low alkyl radical;
$R_{17}$ and $R_{18}$, which may be identical or different, represent hydrogen atoms, halogen atoms or alkyl radicals;
$R_{16}$ and $R_{19}$, which may be identical or different, represent a hydrogen atom, an alkyl, hydroxyalkyl or aminoalkyl radical, wherein the amino moiety may be substituted; Y represents a radical selected from the group constituted by the following radicals:

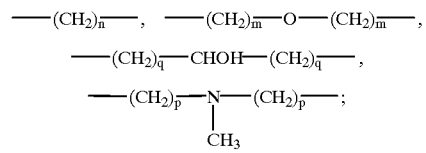

where n is a whole number between 0 and 8 and m, q and p are whole numbers between 0 and 4. This base can also be in the form of addition salts with acids.

The alkyl or alkoxy radicals indicated above preferably represent a group containing one to four carbon atoms, in particular methyl, ethyl, propyl, methoxy and ethoxy.

The following compounds with formula (VI) may be cited:

N,N'-bis-(β-hydroxyethyl) N,N'-bis(4'-aminophenyl) 1,3-diamino 2-propanol,
N,N'-bis-(β-hydroxyethyl) N,N'-bis(4'-aminophenyl) ethylene-diamine,
N,N'-bis-(4-aminophenyl) tetramethylenediamine,
N,N'-bis-(β-hydroxyethyl) N,N'-bis(4-aminophenyl) tetramethylenediamine,
N,N'-bis-(4-methylaminophenyl) tetramethylenediamine,
N,N'-bis-(ethyl) N,N'-bis-(4'-amino 3'-methylphenyl) ethylenediamine.

The following orthoaminophenols may in particular be cited:
ortho-aminophenol,
6-methyl 1-hydroxy 2-aminobenzene,
4-methyl 1-amino 2-hydroxybenzene,
4-acetylamino 1-amino 2-hydroxybenzene.

In a first particular embodiment of the invention, the composition contains the following combination:
at least 3-ethyl p-aminophenol or a salt thereof as an oxidation dye precursor:
at least 2-methyl 5-aminophenol and/or 2-methyl 5-N-(β-hydroxyethyl) aminophenol or a salt thereof as coupler:
at least one metaphenylenediamine with formula (III) as defined above, as additional coupler.

Preferred metaphenylenediamines with formula (III) in this first embodiment are those where groups $R_5$ to $R_8$ represent hydrogen and $R_9$ represents a $C_1$–$C_4$ hydroxyalkoxy or $C_2$–$C_4$ polyhydroxyalkoxy group.

A particularly preferred $C_1$–$C_4$ hydroxyalkoxy radical is the β-hydroxyethyloxy radical.

A particularly preferred $C_2$–$C_4$ polyhydroxyalkoxy radical is the 1,2-dihydroxypropyloxy radical.

The following may in particular be cited:
2,4-diaminophenoxyethanol,
(2,4-diamino)phenyl-α,β-dihydroypropylether,
1-[2',4'-diaminophenoxypropyloxy] 2,4-diamino-benzene,
2-amino 4-N-(β-hydroxyethyl) aminoanisole,
2,4-diaminophenoxyacetic acid,
4,6-bis-(β-hydroxyethoxy) 1,3-diaminobenzene, and salts thereof.

Copper-shaded colours are obtained which are particularly wash resistant.

A second particular embodiment of a composition of the invention contains the following combination:
at least 3-ethyl p-aminophenol or a salt thereof as an oxidation dye precursor;
at least 2-methyl 5-aminophenol and/or 2-methyl 5-N-(β-hydroxyethyl)aminophenol or a salt thereof as coupler;
at least one additional oxidation dye precursor selected from:
the orthoaminophenols described above,
paraphenylenediamines with formula (IV),
bis-phenylalkylenediamines with formula (VI),
paraaminophenols with formula (V).

In this second embodiment, when an orthoaminophenol is used, orthoaminophenol or 4-acetylamino 2-hydroxybenzene or a salt thereof is preferably used. Copper-shaded colours which are particularly wash resistant are obtained.

In this second embodiment of the invention, when a paraphenylediamine with formula (IV) is used, one of the following is preferably used:
paraphenylenediamine,
paratoluylenediamine,
2,6-dimethyl p-phenylenediamine,
2-β-hydroxyethyl p-phenylenediamine,
2-isopropyl p-phenylenediamine,
N,N-di(β-hydroxyethyl)p-phenylenediamine,
4-amino N-(β-methoxyethyl)aniline, or salts thereof.

Red- or copper-shaded colours are obtained which are particular resistant to perspiration.

When bis-phenylalkylenediamine is used in this second embodiment of the invention, N,N'-bis-((β-hydroxyethyl) N,N'-bis-(4'-aminophenyl) 1,3-diamino 2-propanol is preferably used. This also produces red- or copper-shaded colours which are particularly resistant to perspiration.

When a paraaminophenol with formula (V) is used in this second embodiment of the invention, 2-methoxymethyl 4-aminophenol or its addition salt with an acid is preferably used. Red- or copper-shaded colours are thus obtained which have particularly good resistance to various treatments which can be applied to the hair.

Direct dyes may be added to these compositions, as is well known in the art, in particular in order to shade or enrich the colours produced by the oxidation dye precursors. These direct dyes may be azo dyes, anthraquinone dyes or nitrated derivatives of the benzene series.

The total content of ortho and/or para type oxidation dye precursors and couplers used in the dye compositions of the invention preferably constitutes 0.3% to 7% by weight of the total composition weight. The concentration of the compound with formula (I) may be between 0.05% and 3.5% by weight of the total composition weight.

Preferred embodiments of dye compositions in accordance with the invention also contain anionic, cationic, non-ionic or amphoteric surfactants or mixtures thereof. Examples of such surfactants are alkylbenzenesulphonates, alkylnaphthalenesulphonates, sulphates, ethersulphates and fatty alcohol sulphonates, quaternary ammonium salts such as trimethylcetylammonium bromide and cetylpyridinium bromide, fatty acid ethanolamides which may be oxyethylenated, polyglycerolated fatty alcohols, polyoxyethylenated or polyglycerolated alkylphenols and polyoxyethylenated alkylsulphates.

These surfactants are present in compositions in accordance with the invention in proportions of between 0.5% and 55% by weight, preferably between 2% and 50% by weight with respect to the total composition weight.

The compositions may also contain organic solvents to dissolve components which are insufficiently soluble in water. Examples of these solvents are $C_1$–$C_4$ low alcohols such as ethanol and isopropanol; glycerol; glycols or glycol ethers such as 2-butoxyethanol, ethyleneglycol, propyleneglycol, diethyleneglycol monoethylether and monomethylether and aromatic alcohols such as benzyl alcohol or phenoxyethanol and analogous products and mixtures thereof.

The solvents are preferably present in proportions of between 1% and 40% by weight, in particular between 5% and 30% by weight with respect to the total composition weight.

Thickening agents which may be added to compositions of the invention may be selected from sodium alginate, gum arabic, acrylic acid polymers, which may be crosslinked, cellulose derivatives, heterobiopolysaccharides such as xanthane gum, or mineral thickening agents such as bentonite.

The thickening agents are preferably present in proportions of between 0.1% and 5%, in particular between 0.2% and 3% by weight with respect to the total composition weight.

Antioxidising agents which may be present in the compositions are selected from sodium sulphite, thioglycolic acid, sodium bisulphite, dehydroascorbic acid, hydroquinone, 2-methylhydroquinone and homogentisic acid. The antioxidizing agents are present in the composition in proportions of between 0.05% and 1.5% by weight with respect to the total composition weight.

The pH of the compositions is between 4 and 11. It is adjusted to the desired value using alkalising agents which are well known in the art, such as ammonium hydroxide, alkaline carbonates, alkanolamines such as mono-, di- and triethanolamines and derivatives thereof or sodium or potassium hydroxide or conventional acidifying agents such as mineral or organic acids, for example hydrochloric, tartaric, citric, phosphoric and sulphonic acid.

These compositions may also contain other cosmetically acceptable additives such as penetrating agents, sequestrating agents, perfumes, buffers, etc.

Compositions of the invention may be in a number of different forms, such as a liquid, cream, gel or any other form which is suitable for dyeing keratinous fibres, in particular human hair. The compositions may be packaged in aerosol canisters with a propellant and foam forming agent, such as in the form of mousse.

Compounds with formula (I) are used in accordance with the invention in a method which comprises application of the compound with formula (I) to the keratinous fibres, optionally with one or more couplers, and are developed with an oxidising agent.

Dye compositions of the invention containing at least one compound with formula (I) and optionally containing at least one coupler are used in a method involving developing with an oxidising agent.

According to this method, the dye composition described above is mixed just before use with a sufficient amount of an oxidising solution to develop the dye, and the mixture obtained is applied to the keratinous fibres, in particular human hair.

The pH of the composition applied to the hair preferably varies between 3 and 11. It is adjusted to the desired value using alkalising or acidifying agents which are well known in the art, such as those described above. The oxidising solution contains, as the oxidising agent, hydrogen peroxide, urea peroxide, persalts such as ammonium persulphate, organic peracids and their salts or alkali metal bromates. A 20 volume hydrogen peroxide solution is preferably used.

The mixture obtained is applied to the hair and left for 10 to 40 minutes, preferably 15 to 30 minutes, followed by rinsing, shampooing, further rinsing and drying.

The compound with formula (I) as defined above may also be used in a method involving several steps, one step consisting of applying the compound with formula (I) and another step consisting in applying a dye composition containing at least one coupler and/or at least one other oxidation dye precursor different to those with formula (I).

The oxidising agent may be introduced just before application into the composition which is applied in the second step or it may be applied to the keratinous fibres themselves in a third step, the contact time, pH, washing and drying conditions being identical to those described above.

The following examples illustrate the invention.

PREPARATION EXAMPLES

Preparation of 3-hydroxymethyl p-aminophenol

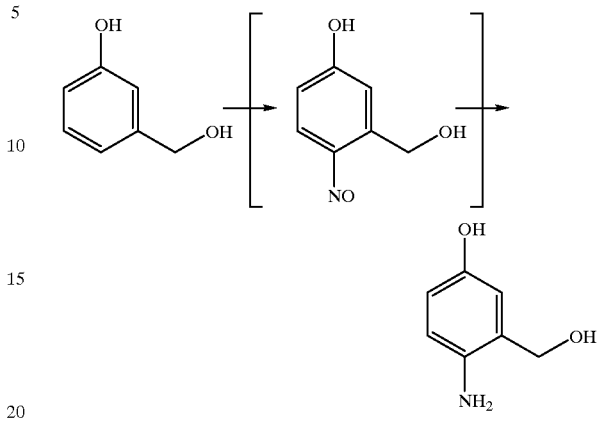

31 g (0.25 mole) of metahydroxybenzyl alcohol was mixed with 10 g of soda, 17.5 g of sodium nitrite and 380 g of ice water.

25 ml of concentrated sulphuric acid was added over 30 minutes at between 0° C. and 5° C.; after one hour, the beige precipitate was filtered off. The wet precipitate was added using a spatula to a solution of 200 g of sodium hydrosulphite in 600 ml of 2.5 N soda at 80–90° C. After 15 minutes this was cooled, acidified with sulphuric acid and treated with 100 g of carbon black. It was then filtered and neutralised with ammonium hydroxide solution. After two hours at room temperature, the precipitate was filtered and taken up in four times 500 ml of ethyl acetate. The organic phases were dried and evaporated. The residue was recrystallised from 95° ethanol.

Beige crystals with a melting point of 171° C. were obtained.

The following was obtained for formula $C_7H_9NO_2$:

| % | C | H | N | O |
|---|---|---|---|---|
| Calculated | 60.93 | 6.47 | 10.07 | 23.02 |
| Found | 60.28 | 6.49 | 10.00 | 23.12 |

Preparation of 3-cyanomethyl p-aminophenol

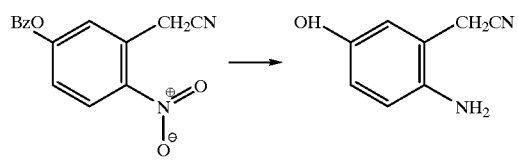

A suspension of 5.4 g of 2-nitro 5-benzyloxyphenylacetonitrile, 5.4 ml of cyclohexene, 22 ml of ethanol and 3 g of 10% palladium on activated charcoal was refluxed for five hours. The suspension was then hot filtered and the filtrate evaporated. The residue was recrystallised from ethanol to produce dark beige crystals.

Melting point: 173° C.

| Elemental analysis for C$_8$H$_8$N$_2$O | | | | |
|---|---|---|---|---|
| % | C | H | N | O |
| Calculated | 64.85 | 5.44 | 18.91 | 10.80 |
| Found | 64.97 | 5.47 | 18.96 | 11.01 |

Preparation of 3-(β-ethoxyethyl)p-aminophenol

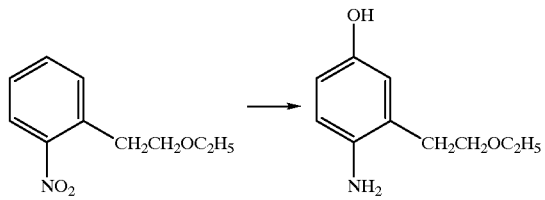

58.5 g (0.3 mole) of 1-(β-ethoxyethyl)2-nitrobenzene was added at a temperature of 90° C. to a solution of 100 ml of concentrated sulphuric acid diluted in 1 litre of distilled water. 17 g of aluminium powder was added using a spatula and with vigourous stirring. Stirring was maintained for 40 minutes and then 70 g of tartaric acid was added. Stirring was continued for a further 15 minutes with the temperature maintained at 90° C. and then the reaction medium was cooled and the suspension filtered through sintered glass. The filtrate was neutralised with 20% ammonium hydroxide at a temperature below 20° C. A pinkish beige precipitate was obtained. The precipitate was taken up in 0.5 l of refluxing ethyl acetate, hot filtered and dry concentrated. It was recrystallised again from ethyl acetate to obtain beige crystals of the expected product which had a melting point of 102° C.

| Elemental analysis for C$_{10}$H$_{15}$NO$_2$ | | | | |
|---|---|---|---|---|
| % | C | H | N | O |
| Calculated | 66.27 | 8.34 | 7.73 | 18.66 |
| Found | 65.88 | 8.32 | 7.51 | 18.30 |

Preparation of 3-(β-methoxyethyl)p-aminophenol

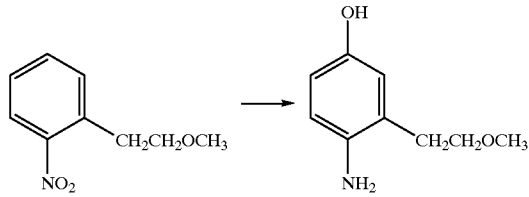

The method of the previous example was followed, starting from 1-(β-methoxyethyl)2-nitrobenzene (54.3 g, i.e. 0.3 mole) and white crystals having a melting point of 82° C. were obtained after recrystallisation from ethyl acetate.

| Elemental analysis for C$_9$H$_{13}$NO$_2$ | | | | |
|---|---|---|---|---|
| % | C | H | N | O |
| Calculated | 64.67 | 7.78 | 8.38 | 19.16 |
| Found | 64.46 | 7.86 | 8.33 | 19.29 |

DYEING EXAMPLES

Dyeing at Basic pH

Example 1 to 6

The following dye composition was prepared:

| Dyes | x g |
|---|---|
| Oleic alcohol glycerolated with 2 moles of glycerol | 5 g |
| Oleic alcohol glycerolated with 4 moles of glycerol | 5 g |
| Oleic acid | 5 g |
| Oleic diethanolamine | 5 g |
| Oleic diethanolamine | 12 g |
| Ethyl alcohol | 10 g |
| 2-ethoxy ethanol | 12 g |
| Sodium metabisulphite in aqueous solution, 35% AM | 1.3 g |
| 2-methylhydroquinone | 0.17 g |
| Ammonium hydroxide solution, 20% NH$_3$ | 10.2 g |
| Water qsp | 100 g |

This composition was mixed just before use with an equal weight of 20 volume hydrogen peroxide solution (6% by weight) with a pH of 3.

This mixture was applied to permed or unpermed grey hair containing 90% white, left for 30 minutes then rinsed out and the hair shampooed. After drying, the hair had been dyed to the shade given in the table below.

| | EXAMPLE | | | | | |
|---|---|---|---|---|---|---|
| | 1 | 2 | 3 | 4 | 5 | 6 |
| 3-ethyl p-aminophenol | 0.685 g | 0.685 g | 0.685 g | | | |
| 3-hydroxy-methyl p-amino-phenol | | | | 0.695 g | 0.695 g | 0.695 g |
| 2-methyl 5-aminophenol | 0.615 g | | | 0.615 g | | |
| 2,4-diamino phenoxy-ethanol | | 1.2 g | | | 1.2 g | |
| 6-hydroxy-indole | | | 0.665 g | | | 0.665 g |
| pH of mixture applied to hair | 10.3 | 10 | 10.2 | 10.3 | 10.1 | 10.3 |
| SHADE OBTAINED | | | | | | |
| Unpermed grey hair, 90% white | | Plum | | | Red chest-nut | |
| Permed grey hair, 90% white | Mid copper chest-nut | | Dark blond | Dark copper | | Dark copper blond |

Examples 7 to 16

The following dye composition was prepared:

| Dyes | x g |
|---|---|
| Oleic alcohol glycerolated with 2 moles of glycerol | 4 g |
| Oleic alcohol glycerolated with 4 moles of glycerol (78% AM) | 5.69 g AM |
| Oleic acid | 3 g |
| Oleic amine with 2 moles of ethylene | 7 g |

-continued

| | |
|---|---|
| oxide, sold by AKZO under the trade name ETHOMEEN O12 | |
| Diethylaminopropyl laurylamino-succinamate, sodium salt, 55% AM | 3 g AM |
| Oleic alcohol | 5 g |
| Oleic acid diethanolamide | 12 g |
| Propyleneglycol | 3.5 g |
| Ethyl alcohol | 7 g |
| Dipropyleneglycol | 0.5 g |
| Propyleneglycol monomethylether | 9 g |
| Sodium metabisulphite, aqueous solution, 35% AM | 0.455 g AM |
| Ammonium acetate | 0.8 g |
| Antioxidising, sequestrating agents | qs |
| Perfume, preservative | qs |
| Ammonium hydroxide solution, 20% NH$_3$ | 10 g |
| Demineralised water qsp | 100 g |

This composition was mixed just before use with an equal weight of 20 volume hydrogen peroxide solution (6% by weight) with a pH of 3.

The mixture was applied to permed or unpermed grey hair with 90% white, left for 30 minutes then rinsed out and the hair shampooed.

After drying, the hair had been dyed to the shade given in the table below.

-continued

| | |
|---|---|
| oxide, sold by AKZO under the trade name ETHOMEEN O12 | |
| Coprah diethanolamide sold by HENKEL under the trade name COMPERLAN KD | 9 g |
| Propyleneglycol | 4 g |
| 2-butoxyethanol | 8 g |
| 96° ethanol | 6 g |
| Pentasodic salt of diethylenetriamine pentacetic acid, sold be PROTEX under the trade name MASQUOL DTPA | 2 g |
| Hydroquinone | 0.15 g |
| Aqueous solution of sodium metabisulphite, 35% AM | 1.3 g |
| Ammonium hydroxide solution, 20% NH$_3$ | 10 g |
| Water qsp | 100 g |

Just before use, 100 g of 20 volume hydrogen peroxide (6% by weight) with a pH of 3 was added. The pH of the mixture was 10. It was applied to unpermed grey hair with 90% white and left for 25 minutes at a temperature of 30° C. After shampooing and rinsing, this mixture produced an ash beige colour.

Dyeing at acid pH

| EXAMPLE | 7 | 8 | 9 | 10 | 11 | 12 | 13 | 14 | 15 | 16 |
|---|---|---|---|---|---|---|---|---|---|---|
| 3-ethyl p-aminophenol | 0.41 g | 1.0 g | 1.3 g | 0.8 g | 2.2 g | 1.0 g | | | | |
| 3-tert-butyl p-aminophenol | | | | | | | 0.3 g | 0.4 g | | |
| 3-(β-ethoxyethyl)p-aminophenol | | | | | | | | | 0.7 g | |
| 3-(β-methoxyethyl)p-aminophenol | | | | | | | | | | 0.76 g |
| 2-methyl 5-aminophenol | | 1.2 g | | | 3.0 g | 1.2 g | 0.5 g | | | 0.55 g |
| 2-methyl 5-N-(β-hydroxyethyl) aminophenol | 0.50 g | | 2.0 g | 1.4 g | | | | 0.8 g | 0.65 g | |
| 2,4-diaminophenoxyethanol, 2 HCl | | 0.67 g | | | | | | | | |
| 2-methoxymethyl 4-aminophenol | | | 0.3 g | | | | | | | |
| N,N'-bis-(β-hydroxyethyl)N,N'-bis-(4'-aminophenyl)1,3-diamino 2-propanol | | | | 0.2 g | | | | | | |
| p-phenylenediamine | | | | | 0.3 g | | | 0.1 g | | |
| 2,6-dimethyl p-phenylenediamine, 2 HCl | | | | | | | 0.3 g | | | |
| Ortho-aminophenol | | | | | | 0.3 g | | | | |
| pH of mixture applied to hair | 9.8 | 9.7 | 9.6 | 9.7 | 9.7 | 9.6 | 9.7 | 9.7 | 10.7 | 10.7 |
| SHADE OBTAINED | | | | | | | | | | |
| on unpermed grey hair with 90% white | | Ash high-lights | | Light copper high-lights | | Golden copper | Ash high-lights | | | Very light copper high-lighted blond |
| on permed grey hair with 90% white | High-lighted copper blond | | Deep copper | | High-lighted red | | | Red high-lights | Light copper high-lighted blond | |

Example 17

The following dye composition was prepared:

| | |
|---|---|
| 3-cyanomethyl p-aminophenol | 0.37 g |
| 2-metyl 5-N-(β-hydroxyethyl) aminophenol | 0.41 g |
| Oleic alcohol glycerolated with 2 moles of glycerol | 4.5 g |
| Oleic alcohol glycerolated with 4 moles of glycerol | 4.5 g |
| Oleic amine with 2 moles of ethylene | 4.5 g |

Example 18

The following dye composition was prepared:

| | |
|---|---|
| 3-ethyl p-aminophenol | 0.41 g |
| 2-hydroxy 4-N-(β-hydroxyethyl) aminoanisole | 0.768 g |
| Oleic alcohol polyglycerolated with 2 moles of glycerol | 4 g |
| Oleic alcohol polyglycerolated with 4 moles of glycerol (78% AM) | 5.69 g AM |

17
-continued

| | |
|---|---|
| Oleic acid | 3 g |
| Oleic amine with 2 moles of ethylene oxide, sold by AKZO under the trade name ETHOMEEN O12 | 7 g |
| Diethylamainopropyl laurylamino-succinamate, sodium salt, 55% AM | 3 g AM |
| Oleic alcohol | 5 g |
| Oleic acid diethanolamide | 12 g |
| Propyleneglycol | 3.5 g |
| Ethyl alcohol | 7 g |
| Dipropyleneglycol | 0.5 g |
| Propyleneglycol monomethylether | 9 g |
| Sodium metabisulphite, aqueous solution, 35% AM | 0.455 g AM |
| Ammonium acetate | 0.8 g |
| Antioxidising, sequestrating agents | qs |
| Perfume, preservative | qs |
| Monoethanolamine qsp pH = | 9.8 |
| Demineralised water qsp | 100 g |

Just before use, the composition was mixed with a 20 volume hydrogen peroxide (6% by weight) solution and the pH was adjusted to between 1 and 1.5 using 2.5 g of orthophosphoric acid per 100 g of hydrogen peroxide.

The pH of the mixture was 6.5.

The mixture was applied to permed grey hair with 90% white and left for 30 minutes.

The hair was then rinsed, shampooed and dried. It had been dyed a very light slightly golden blond.

Example 19

The following dye composition was prepared:

| | |
|---|---|
| 3-hydroxymethyl p-aminophenol | 0.9 g |
| 2-methyl 5-aminophenol) | 1.2 g |
| p-phenylenediamine | 0.3 g |
| Oleic alcohol polyglycerolated with 2 moles of glycerol | 4 g |
| Oleic alcohol polyglycerolated with 4 moles of glycerol (78% AM) | 5.69 g AM |
| Oleic acid | 3 g |
| Oleic amine with 2 moles of ethylene oxide, sold by AKZO under the trade name ETHOMEEN O12 | 7 g |
| Diethylamainopropyl laurylamino-succinamate, sodium salt, 55% AM | 3 g AM |
| Oleic alcohol | 5 g |
| Oleic acid diethanolamide | 12 g |
| Propyleneglycol | 3.5 g |
| Ethyl alcohol | 7 g |
| Dipropyleneglycol | 0.5 g |
| Propyleneglycol monomethylether | 9 g |
| Sodium metabisulphite, aqueous solution, 35% AM | 0.455 g AM |
| Ammonium acetate | 0.8 g |
| Antioxidising, sequestrating agents | qs |
| Perfume, preservative | qs |
| Monoethanolamine qsp pH = | 9.8 |
| Demineralised water qsp | 100 g |

Just before use, the composition was mixed with an equal weight of 20 volume hydrogen peroxide (6% by weight) solution and the pH was adjusted to between 1 and 1.5 using 2.5 g of orthophosphoric acid per 100 g of hydrogen peroxide.

The pH of the mixture was 6.8.

The mixture was applied to unpermed grey hair with 90% white and left for 30 minutes.

The hair was then rinsed, shampooed and dried. It had been dyed blond with dark auburn highlights.

18

We claim:

1. Dye composition for keratinous fibres, comprising, in an aqueous dye medium, an amount effective for oxidation dyeing said fibres of at least one 3-substituted para-aminophenol as an oxidation dye precursor, said compound having the formula:

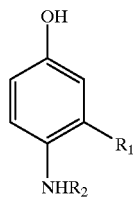

(I)

wherein $R_1$ represents a $C_1$–$C_4$ alkyl radical, a $C_2$–$C_4$ alkenyl radical, a $C_1$–$C_6$ monohydroxyalkyl, a $C_2$–$C_6$ polyhydroxyalkyl radical, a $C_2$–$C_6$ alkoxyalkyl radical, a $C_1$–$C_4$ cyanoalkyl radical, a $C_1$–$C_4$ halogenoalkyl radical, an aminoalkyl radical having the formula:

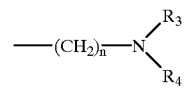

(II)

where:
  n is a whole number from 1 to 6 inclusive;
  $R_3$ and $R_4$, which may be identical or different, represent a hydrogen atom or a $C_1$–$C_4$ alkyl radical, a $C_1$–$C_4$ hydroxyalkyl radical or a $C_1$–$C_6$ acyl radical;
  $R_2$ represents a hydrogen atom, a $C_1$–$C_6$ alkyl radical, a $C_1$–$C_6$ monohydroxyalkyl radical or a $C_2$–$C_6$ polyhydroxyalkyl radical, provided that:
    when $R_2$ is hydrogen, $R_1$ does not represent methyl or trifluoromethyl,
  or an addition salt thereof with an acid.

2. Dye composition according to claim 1, wherein the 3-substituted para-aminophenol is 3-ethyl p-aminophenol, 3-hydroxymethyl p-aminophenol, 3-cyanomethyl p-aminophenol, 3-tert-butyl p-aminophenol, 3-(β-methoxyethyl) p-aminophenol, 3-(β-ethoxyethyl) p-aminophenol or a salt thereof.

3. Dye composition according to claim 1, wherein the composition further contains an effective amount of one or more couplers which are metadiphenols, metaaminophenols, metaphenylenediamines, metaacylaminophenols, metaureidophenols, metacarbalkoxyaminophenols, α-naphthol, indole derivatives, β-ketone compounds or pyrazoles.

4. Dye composition according to claim 1, wherein the composition further contains an effective amount of at least one para or ortho oxidation dye precursor which is a paraphenylenediamine, a para-aminophenol other than those with formula (I), a para heterocyclic derivative of pyridine or pyrimidine, an orthoaminophenol or a bis-phenylalkylenediamine.

5. Dye composition according to claim 1, wherein the composition contains 3-ethyl p-aminophenol or a salt thereof as an oxidation dye precursor, at least one coupler which is 2-methyl 5-aminophenol or 2-methyl 5-N-(β-hydroxyethyl) aminophenol or a salt thereof and at least one metaphenylenediamine or a salt thereof to act as an additional coupler.

6. Dye composition according to claim 1, wherein the composition contains 3-ethyl p-aminophenol or a salt thereof as an oxidation dye precursor, at least one coupler which is 2-methyl 5-aminophenol or 2-methyl 5-N-(β-hydroxyethyl) aminophenol or a salt thereof and an additional oxidation dye precursor which is an orthoaminophenol, a paraphenylenediamine, a bisphenylalkylenediamine or a para-aminophenol other than those with formula (I).

7. Dye composition according to claim 1, wherein the composition contains 0.05% to 3.5% by weight with respect to the total composition weight of the at least one 3-substituted para-aminophenol.

8. Dye composition according to claim 1, wherein the composition contains a total of 0.3% to 7% by weight with respect to the total composition weight of ortho and para oxidation dye precursors and couplers.

9. Dye composition according to claim 1, wherein the composition further contains at least one additive which is an anionic, cationic, nonionic or amphoteric surfactant or a mixture thereof, in proportions of between 0.5% and 55% by weight, an organic solvent in concentrations of between 1% and 40% by weight, a thickening agent in proportions of between 0.1% and 5% by weight, an antioxidising agent in proportions of between 0.05% and 1.5% by weight, a direct dye, a penetrating agent, a sequestrating agent, a perfume or buffer, the percentages by weight being with respect to the total composition weight.

10. Dye composition according to claim 1, wherein the composition is in the form of a liquid, cream, gel or mousse and has a pH of between 4 and 11.

11. A method of oxidation dyeing keratinous fibres, comprising applying to the fibres an effective amount for dyeing said fibres of at least one 3-substituted p-aminophenol as an oxidation dye precursor, said compound having the formula:

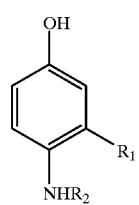

(I)

wherein $R_1$ represents a $C_1$–$C_4$ alkyl radical, a $C_2$–$C_4$ alkenyl radical, a $C_1$–$C_6$ monohydroxyalkyl, a $C_2$–$C_6$ polyhydroxyalkyl radical, a $C_2$–$C_6$ alkoxyalkyl radical, a $C_1$–$C_4$ cyanoalkyl radical, a $C_1$–$C_4$ halogenoalkyl radical, an aminoalkyl radical having the formula:

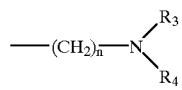

(II)

where:
  n is a whole number from 1 to 6 inclusive;
  $R_3$ and $R_4$, which may be identical or different, represent a hydrogen atom or a $C_1$–$C_4$ alkyl radical, a $C_1$–$C_4$ hydroxyalkyl radical or a $C_1$–$C_6$ acyl radical;
  $R_2$ represents a hydrogen atom, a $C_1$–$C_6$ alkyl radical, a $C_1$–$C_6$ monohydroxyalkyl radical or a $C_2$–$C_6$ polyhydroxyalkyl radical, provided that:

when $R_2$ is hydrogen, $R_1$ does not represent methyl or trifluoromethyl, or an addition salt thereof with an acid, optionally in the presence of one or more couplers, wherein a color is developed by application of an oxidising agent.

12. Method according to claim 11, wherein the 3-substituted para-aminophenol is 3-ethyl p-aminophenol, 3-hydroxymethyl p-aminophenol, 3-cyanomethyl p-aminophenol, 3-tert-butyl p-aminophenol, 3-(β-methoxyethyl)p-aminophenol or 3-(β-ethoxyethyl) p-aminophenol.

13. Method according to claim 11, wherein the 3-substituted para-aminophenol with formula (I) according to claim one or more couplers are metadiphenols, metaaminophenols, metaphenylenediamines, metaacylaminophenols, metaureidophenols, metacarbalkoxyaminophenols, α-naphthol, indole derivatives, β-ketone compounds or pyrazoles.

14. Method according to claim 11, wherein a dye composition containing the at least one 3-substituted para-aminophenol and optionally at least one coupler in an aqueous dye medium is mixed just before application with a sufficient quantity of oxidising solution to develop a color, the pH of the resulting composition varying from 3 to 11, and the mixture thus produced is applied to the keratinous fibres, left on said fibers for 10 to 40 minutes and then rinsed out, after which said fibres are shampooed, rinsed again and dried.

15. Method according to claim 11, wherein the at least one 3-substituted para-aminophenol is applied in a first step to the keratinous fibres, and in a second step a dye composition containing at least one coupler or at least one other oxidation dye precursor other than that with formula (I) is applied to the keratinous fibres, color is developed with an oxidising agent present in the composition applied in the second step, or applied to the keratinous fibres in a third step, the resulting composition is left on said fibers for 10 to 40 minutes and then rinsed out, after which the fibres are shampooed, rinsed again and dried.

16. 3-Substituted para-aminophenol with formula:

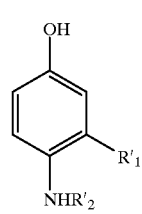

(1')

where $R'_1$ represents a cyano radical;

$R'_2$ represents a $C_1$–$C_6$ alkyl radical, a $C_1$–$C_6$ monohydroxyalkyl radical or a $C_2$–$C_6$ polyhydroxyalkyl radical;

or an addition salt thereof with an acid.

* * * * *